US006491914B1

(12) United States Patent
Vázguez López et al.

(10) Patent No.: US 6,491,914 B1
(45) Date of Patent: Dec. 10, 2002

(54) ANTI-IDIOTYPIC MONOCLONAL ANTIBODIES, THEIR USE IN THE ACTIVE IMMUNOTHERAPY OF MALIGNANT TUMORS, AND COMPOSITIONS INCLUDING THE ANTI-IDIOTYPIC MONOCLONAL ANTIBODIES

(75) Inventors: Ana Maria Vázguez López, Habana; Rolando Pérez Rodriguez, Vibora; Eladio Iglesis Guerra, Habana; Alexis Pérez, Habana; Gumersinda Bombino Lopez, Habana; Irene Beausoleil Delgado, Habana, all of (CU)

(73) Assignee: Centro de Inmunologia Molecular, Habana (CU)

( * ) Notice: Subject to any disclaimer, the term of this patent is extended or adjusted under 35 U.S.C. 154(b) by 0 days.

(21) Appl. No.: 09/448,883

(22) Filed: Nov. 24, 1999

Related U.S. Application Data

(60) Division of application No. 09/015,540, filed on Jan. 29, 1998, now Pat. No. 6,063,379, which is a continuation-in-part of application No. 08/353,560, filed on Dec. 9, 1994, now Pat. No. 5,817,513.

(30) Foreign Application Priority Data

Dec. 9, 1993 (CU) ............................................. 114/93
Oct. 21, 1997 (CU) ............................................. 119/97

(51) Int. Cl.[7] ...................... A61K 39/395; A61K 45/00; A61K 47/00

(52) U.S. Cl. ................. 424/130.1; 424/131.1; 424/138.1; 424/141.1; 424/152.1; 424/155.1; 424/156.1; 424/172.1; 424/174.1; 424/278.1

(58) Field of Search ........................... 424/130.1, 131.1, 424/138.1, 141.1, 152.1, 155.1, 156.1, 172.1, 174.1, 278.1

(56) References Cited

U.S. PATENT DOCUMENTS 5,208,146 A  *  5/1993  Reiko
5,419,904 A  *  5/1995  Irie

OTHER PUBLICATIONS

Boon (Adv. Can Res, 58:177–210 ), 1992.*
Gura (Science, 278:1041–1042), 1997.*
Chatterjee et al (Cancer Immunol. Immunother., 38:75–82), 1994.*
Scennerholm (in Progress in Brain Research, 101:xi–xxiv), 1992.*

* cited by examiner

Primary Examiner—Susan Ungar
(74) Attorney, Agent, or Firm—TraskBritt

(57) ABSTRACT

An anti-idiotypic monoclonal antibody that is specific against the N-glycolyl residues of gangliosides, particularly those expressed by cancer cells. The monoclonal antibody is useful as an immunomodulator for cancer treatment. Specifically, the anti-Id monoclonal antibody of the present invention is capable of inducing a predominant anti-idiotypic response in xenogeneic models. The anti-idiotypic monoclonal antibody also exerts a protective effect against malignant tumors in animals.

2 Claims, 8 Drawing Sheets

ANTI-IDIOTYPIC MONOCLONAL ANTIBODIES, THEIR USE IN THE ACTIVE IMMUNOTHERAPY OF MALIGNANT TUMORS, AND COMPOSITIONS INCLUDING THE ANTI-IDIOTYPIC MONOCLONAL ANTIBODIES

RELATED APPLICATION

This patent application is a divisional patent application of U.S. patent application Ser. No. 09/015,540 filed Jan. 29, 1998, now U.S. Pat. No. 6,063,379, which is a continuation in part of application Ser. No. 08/353,560, filed Dec. 9, 1994, Now U.S. Pat. No. 5,817,513 the contents of the entirety of both of which is hereby incorporated by this reference.

TECHNICAL FIELD

The present invention relates generally to anti-idiotypic monoclonal antibodies and their use as immunomodulators. More particularly, the present invention involves a murine monoclonal antibody which was developed against a murine monoclonal antibody reactive with N-glycolyl containing gangliosides and with antigens expressed in cancer cells; and its inhibitory effect on tumor growth.

BACKGROUND

One of the strategies for the treatment of cancer has been the use of active immunotherapy, a treatment modality that has the objective of activating the natural potential of the immune system of the host against the tumor.

Since Niels Jerne proposed his idiotypic network theory in 1974 (Jerne, N. K. 1974. *Ann. Inimunol.* 125C, 373–389), new possibilities have emerged in the study of effective therapies against cancer. Jerne's theory presented, for the first time, the immune system as a network of antibodies which can interact with each other and with a large number of natural epitopes, through their variable regions or idiotypes. (Id,) This complex set of idiotype-anti-idiotype interactions operate to regulate immune responses to antigens. Those antibodies made in response to the original antigen, which are typically referred to as Ab1, themselves become antigens and elicit the production of a second set of antibodies, which are typically referred to as anti-idiotype antibodies or Ab2, which may also be regulated by other antibodies that are typically referred as anti-anti-idiotype or Ab3.

The original theory of Jerne continues to be reviewed. It has been reported that the result of the interaction of Ab2 with lymphocytes bearing Ab1 does not necessarily suppress the immune response, but it may also stimulate the immune response. Moreover, Jerne limited his theory to B lymphocytes and antibodies, but it is now clear that T cells play an important role in the regulation of the immune response through the idiotypes of T cell receptors (Teitelbaum, D. et al, 1984 *J. Immunol* 132, 1282–1285, Zanetti, M, et al. (1986) *J. Immunol.* 137, 3140–3196; Powell, J. et al. (1988) 140, 3266–3272; Baskin, J.G. et al. (1990) *J. Immunol.* 145, 202–208; Furuyama, A. et al. (1992) Anticancer Res. 12, 27–32; Raychaudhuri, S. et al. *J. Immunol.* 131, 271–278; Raychaudhuri et al. (1987) *J. Immunol.* 139, 3902–3910, Durrant et al. (1994) *Cancer Res.* 54, 4837–4840).

An idiotype is immunologically defined by reactivity with more than one anti-idiotype that recognizes an idiotypic determinant or idiotope within a given idiotype. Thus, as a particular Ab1 expresses multiple idiotopes, when this Ab1 was administered to syngeneic animals, a heterogeneous population of idiotypic antibodies is obtained.

Classification of the anti-idiotype antibodies focuses on their binding within the antigen-binding site or to some other region of the idiotype. If the binding of the Ab2 with the Ab1 is inhibited by the relevant antigen and if the Ab2 is also capable of inducing an antibody response of the same specificity as the Ab1, it mimics the natural antigen and is classified as Ab2β; this type of Ab2 is referred to as internal image anti-idiotype and can act as a surrogate antigen. Anti-idiotypes that are not inhibited by antigen are designated Ab2α. Ab2α. react with Ab1 idiotopes which are not structurally related with the antigen-binding site. In 1984 Bona and Köhler proposed a third type of anti-idiotype antibodies (Ab2γ), which are inhibited by antigen because of steric interference, this type of anti-idiotype reacts with idiotopes structurally associated with the antigen-binding site, but they do not mimic the antigenic epitope recognized by the Ab1 (Bona and Köhler (1984) Anti-idiotypic antibodies and internal image, in Monoclonal and anti-idiotypic antibodies: Probes for receptor structure and function, Venter J.C., Frasser, C.M., Lindstrom, J. (Eds.) N.Y., Alan R. Liss, pp 141–149, 1984).

Based on Jerne's theory, two main approaches have been developed in the development of vaccines to a large number of antigens, including tumor-associated antigens. The first approach is based on the presentation of epitopes in a different molecular environment, using Ab2 β. Vaccines containing this type of anti-idiotype antibodies have been able to induce protective responses against viruses, bacteria, and parasites (Kennedy et al. (1986) 232, 220–223; 1047; McNamara et al. (1985) *Science* 226, 1325–1326). Ab2β have also been used to induce immune responses to tumor-associated antigens and positive results have been obtained in animal models and in clinical trials (Raychauhuri et al. (1986) *J. Immunol.* 137, 1743–1749; Raychauhuri et al. (1987) *J. Immunol.* 139, 3902–3910; Bhattacharya-Chatterjee et al. (1987) *J. Immunol.* 139, 1354–1360; Bhattacharya-Chatterjee et al. (1988) *J. Immunol.* 141, 1398–1403; Herlyn, D. et al. (1989) *Intern. Rev. Immunol.* 4, 347–357; Chen, Z-J et al. *Cell Imm. Immunother. Cancer* (1990) 351–359; Herlyn, D. et al. (1991) *In Vivo* 5, 615–624; Furuya et al. (1992) *Anticancer Res.* 12, 27–32; Mittelman, A. et al. (1992) *Proc. Natl. Acad. Sci., USA* 89, 466–470; Durrant, L. G. et al. (1994) *Cancer Res.* 54, 4837–4840; Mittelman, A. et al. (1994) *Cancer Res.* 54, 415–421; Schmitt, H. et al. (1994) *Hybridoma* 13, 389–396; Chakrobarty, M. et al. (1995) *J. Immunother.* 18, 95–103; Chakrobarty, M. et al. (1995) *Cancer Res.* 55, 1525–1530; Foon, K. A. et al. (1995) *Clin. Cancer Res.* 1, 1205–1294; Herlyn, D, et al. (1995) *Hybridoma* 14, 159–166; Sclebusch, H. et al. (1995) *Hybridoma* 14, 167–174; Herlyn, D. et al. (1996) *Cancer Immunol. Immunother.* 43, 65–76). Nevertheless, it has been demonstrated that the β character of an Ab2 is not enough to predict the biological effect that could induce the Ab2 (Raychauhuri et al. (1986) *J. Immunol.* 137, 1743–1749; Raychauhuri et al. (1987) *J. Immunol* 139, 231–278; Maruyama et al. (1996) *Int. J. Cancer* 65, 547–553).

The second approach is based on network manipulation through regulatory idiotypes that do not bind to antigens, but involucrate idiotopes shared with other antibodies or T cells. Evidence that these anti-idiotype antibodies are also able to produce immune responses and protective effects has been accumulated (Paul, W. E. and Bona, C. (1982) *Immunology Today* 3, 230–234; McNamara M. K. et al. (1985) *Science* 226, 1325–1326; Kohler y cols (1992) Proc. 8th Inter. Cong. Immunol. Budapest, pp. 619).

Gangliosides are glycosphingolipids that contain sialic acid and are expressed in the majority of mammalian cell membranes. Although these antigens are present in normal tissues, they can be found in larger quantities and expressed in a different organization and conformation on the surface of malignant cells (Hakomori, S. (1985), *Cancer Res.* 45, 2405–2415; Miraldi, F. (1989) *Seminars in Nuclear Medicine* XIX, 282–294; Hamilton et al. (1993) *Int. J. Cancer* 53, 1–81).

Although gangliosides are useful targets for immune responses, their immunogenicity is extremely poor, due to their carbohydrate nature and their self-antigen condition (Livingston, P. et al, (1995) *Seminars in Cancer Biology* 6, 357–366).

The N-glycolyl variant of sialic acid is expressed in normal tissues of most mammals, but it is very difficult to detect it in normal human tissues (Watarai, S. et al. (1995) *J. Biochem.* 117, 1062–1069. On the other hand, the presence of these antigens has been reported in colon cancer, melanoma, retinoblastoma and breast cancer, among others (Higachi, H. et al. (1984) *Jpn. J. Cancer Res.* (Gann) 75, 1025–1029; Higachi, H. et al. (1985) Cancer Res. 45, 3796–3802; Hirabayashi, I. et al. (1987) Jpn. J. Cancer Res. (Gann) 78, 1614–1620, Higachi, H. et al. (1980) Jpn. J. Cancer Res. (Gann) 79, 952–956, Miyake, M. et al. (1990) *Cancer* 65, 499–505; Devine, P. L. et al. (1991) *Cancer Res.* 51,5826–5306; Vázquez, A. M. et al. (1995) *Hybridoma* 14,551–556; Marquina, G. et al. (1996) *Cancer Res.* 56, 5165–5171).

Immunization with vaccines which contain gangliosides has resulted in the prolonged survival of melanoma patients who developed anti-ganglioside antibodies (Livingston, P. et al. (1987) *Proc. Natl. Acad. Sci. USA* 84, 2911–2915, Livingston, P. et al. (1989) *Cancer Res.* 49, 7045–7050; Livingston, P. (1995) *Immunological Reviews* 145, 147–166). Nevertheless, the problems of the antigens, together with their poor immunogenicity, have made the use of idiotypic antibodies an attractive alternative for active immunotherapy in this antigenic model.

A murine anti-idiotype monoclonal antibody (4C10) was generated against a human IgM monoclonal antibody (L612) that recognizes GM3 on human melanoma. Sera of mice immunized with this anti-idiotype monoclonal antibody coupled with keyhole limpet hemocyanin (KLH) reacted strongly with an antigen-positive melanoma cell line and with purified GM3, which suggested that this anti-idiotype monoclonal antibody which carries the internal image of GM3 (Ab2β) may be an effective tool for active specific immunotherapy in patients with melanoma (Yamamoto, S. et al. (1990) *J. Natl. Cancer. Inst.* 82, 1757–1760; Irie, R. F. U.S. Pat. No. 5,208,146). The $V_L$ and $V_H$ from this anti-idiotype monoclonal antibody have been cloned, sequenced and expressed as a chimeric mouse/human IgG1 antibody (Hastings, A. et al. (1992) *Cancer Res.* 52, 1681–1686).

Also, an alpha-type anti-idiotype monoclonal antibody that is useful in immunodiagnostic procedures was generated against the human monoclonal antibody 1612 (Irie, R. F., U.S. Pat. No. 5,208,146).

The monoclonal antibody BEC-2, a murine anti-idiotype monoclonal antibody raised against a mouse monoclonal antibody recognizing the GD3 ganglioside (mAbR24), can mimic GD3 and induce antibodies against this ganglioside despite expression of GD3 on normal rabbit tissue (Chapman, P. B. and Houghton, A. N. (1991) *J. Clin. Invest.* 88, 186–192), The results of a pilot study showed that BEC-2 plus BCG adjuvant significantly increased the survival of patients with small cell lung cancer (*Scrip Magazine* (1996) pp. 56–59; 33rd *American Society of Clinical Oncology annual meeting* (1997)).

The immunization of rats with a murine monoclonal antibody specific against GD2 (3F8) generated anti-idiotype monoclonal antibodies which, when tested as immunogens in mice, could stimulate antibodies that reacted with ganglioside GD3. It was suggested that these anti-idiotype monoclonal antibodies might be useful in vaccine construction (Cheung, N-K. V. et al. (1993) *Int. J. Cancer* 54, 499–505).

Also, a human anti-idiotype monoclonal antibody was generated using peripheral blood mononuclear cells from a patient that was treated with the murine monoclonal antibody 14G2 specific against GD2. The immunization of rabbits with this human anti-idiotype monoclonal antibody induced anti-GD2 antibodies and a DTH response to antigen-positive tumor cells. It was suggested that this antibody could potentially be used as a human anti-idiotype vaccine in patients with malignant melanoma (Saleh, M. N. et al. (1993) *J. Immunol* 151, 3390–3398).

As is apparent from this background, until now, no anti-idiotype monoclonal antibody has been generated against monoclonal antibodies which recognize N-glycolyl containing-gangliosides. Moreover, no non-beta anti-idiotype monoclonal antibodies in ganglioside models have been described which have an anti-tumoral effect, rather, all previous works claim antigen-surrogate anti-idiotype monoclonal antibodies.

DISCLOSURE OF THE INVENTION

The present invention relates generally to anti-idiotypic or anti-idiotype (anti-Id) monoclonal antibodies (mAbs) and their use as immunomodulators for cancer treatment. More particularly, the present invention involves a murine anti-idiotype monoclonal antibody which was developed against a murine monoclonal antibody that reacts with N-glycolyl containing gangliosides and with antigens expressed in cancer cells.

In accordance with the present invention, the invention provides a new anti-idiotype monoclonal antibody capable of inducing a predominant anti-idiotypic response in xenogenetic models and to exert a protective effect in mice or other animal species bearing malignant tumors.

More specifically, the invention includes a murine anti-idiotype monoclonal antibody raised against a murine anti-N-glycolyl containing-gangliosides antibody.

Preferably, the murine anti-idiotypic monoclonal antibody is one wherein the murine anti-Nlycolyl monoclonal antibody used as an immunogen is a monoclonal antibody produced by the hybridoma deposited under the accession number ECACC 94113026. This murine anti-idiotypic monoclonal antibody preferably induces a predominant anti-idiotypic response in xenogeneic animals and also exerts a protective effect against tumors. This murine anti-idiotypic monoclonal antibody is preferably the gamma-type immunoglobulin herein more specifically identified as 1E10, which is deposited under the accession number ECACC 97112901.

The invention also includes pharmaceutical compositions which contain a pharmaceutically effective amount of the inventive anti-idiotypic monoclonal antibody, together with a carrier selected from the group of carriers consisting of diluents, adjuvants, and transporting molecules. Such a pharmaceutical composition may be useful in the treatment of malignant neoplasias.

BEST MODE OF THE INVENTION

Figure 1:
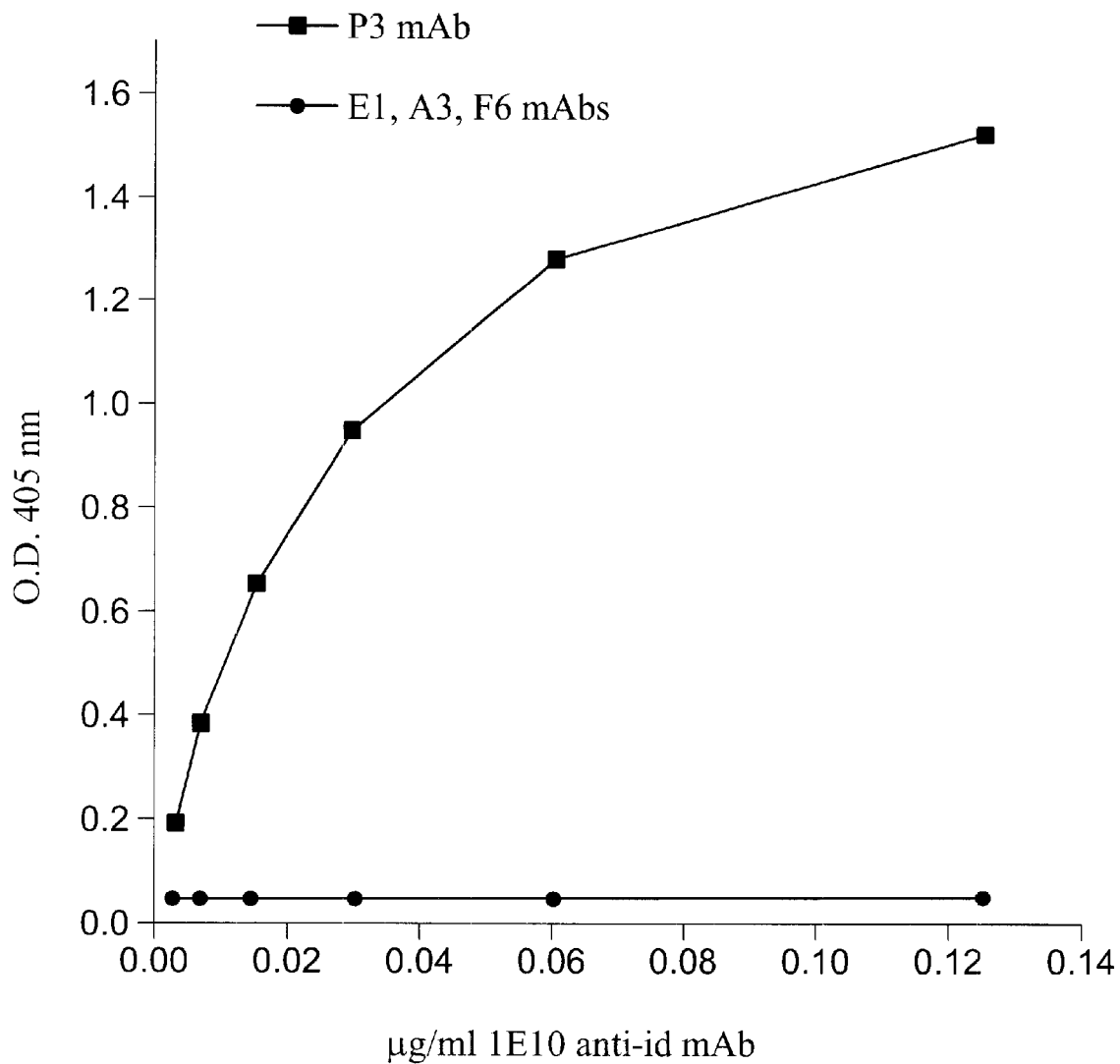
FIG. 1 shows the reactivity of 1E10anti-idiotype P3 monoclonal antibody against P3, E1, A3 and F6 anti-ganglioside monoclonal antibodies.

A. Immunization Procedure for Obtaining Anti-Idiotypic (Ab2) Antibody Response to Antiganglioside Monoclonal Antibodies Mice and other mammalian species are immunized with 25–200 µg doses of purified anti-ganglioside monoclonal antibodies with or without adjuvant and, optionally, coupled to a transporting protein.

Animals receive 2–6 doses of anti-ganglioside monoclonal antibodies at 14 to 30 day intervals be teen doses. Possible immunization routes are intraperitoneal, subcutaneous, intravrenous or a combination of these.

Before and during the immunization period, animal blood serum samples are taken and the Ab2 antibody level response is determined by any known immunoassay methods. Animal serum dilutions are incubated with the anti-ganglioside monoclonal antibody used as the immunogen, or other anti-ganglioside monoclonal antibodies that are not used in the immunization protocol.

Experiments were also performed to define the capacity of the serum of the immunized animals for blocking the binding of the anti-ganglioside monoclonal antibody used as the immunogen to its antigen.

B. Anti-Idiotypic Monoclonal Antibody Production Against Anti-Ganglioside Monoclonal Antibodies (mAbs)

Mice with high Ab2 antibody titers receive a re-immunization with the monoclonal antibody used as the immunogen three days before obtaining the antibody producing cells. Spleen cells should be preferentially used, although other antibody producing cells may be selected.

These cells are fused with myeloma cells that give the hybrid cells or hybridomas the property of in vitro and in vivo reproduction. Cellular fusion may be performed by any of the known methods.

The antibodies produced by the hybridomas are tested by immunoassay methods, preferably by an immuno-enzymatic assay in which hybridoma supernatants are incubated with the monoclonal antibody used as immunogen and with other anti-ganglioside monoclonal antibodies that were not used in the immunizations.

The capacity of the hybridoma supernatant to block the binding of the anti-ganglioside monoclonal antibody used as the immunogen to its antigen is determined by incubating the supernatant with adequate dilutions of the anti-ganglioside monoclonal antibody, followed by incubation of the antibody with its antigen.

The selected hybridomas are cloned at least twice and the resultant monoclonal antibodies are produced in vitro and in vivo, as described above.

The anti-idiotypic. monoclonal antibodies obtained recognize the anti-ganglioside monoclonal antibodies and may possess the capacity to block the binding of the anti-ganglioside monoclonal antibody to its antigen.

C. Immunization Procedure for Obtaining Anti-Anti-Idiotypic (Ab3) Antibody Response to Ab2 Monoclonal Antibodies in Xenogeneic Models Monkeys or other xenogeneic species are immunized with anti-idiotypic monoclonal antibodies. These monoclonal antibodies can be administered with or without adjuvant and optionally coupled to a transporting protein before being used as an immunogen.

Each animal received from 2 to 8 doses of 250 µg to 2 mg of the anti-idiotypic monoclonal antibody at time intervals of 7 to 30 days between doses.

Immunization routes can be intradermal, subcutaneous, intravenous, intraperitoneal or a combination of these.

Animal blood samples are obtained before and during the immunization protocol. The presence of an Ab3 antibody response is monitored using any of the known immunoassay methods.

The administration of anti-idiotypic monoclonal antibody, produced by immunization with anti-ganglioside monoclonal antibodies, to animals can induce a predominant antibody response against the idiotype of the anti-idiotypic monoclonal antibody used as the immunogen, without the induction of an antigen-specific antibody response.

D. Anti-Tumoral Effect of Anti-Idiotypic Monoclonal Antibodies Treatment

Anti-idiotypic monoclonal antibodies are administered in an effective quantity with or without adjuvants and optionally coupled to a transporting protein before being used. The term effective quantity should be understood as meaning an amount of the anti-idiotypic monoclonal antibody that is required to achieve an anti-tumoral effect. The treatment with the anti-idiotypic monoclonal antibodies may be done prior to or after the experimental administration of malignant cells in animals.

Animals receive 1–5 doses of 10–200 µg of the anti-idiotypic monoclonal antibodies at time intervals of 7–30 days between doses.

Immunization routes can be intradermal, intraperitoneal, subcutaneous, intravenous or a combination of these.

After the treatment with the anti-idiotypic monoclonal antibodies, the tumor incidence and the survival in the group treated with the anti-idiotypic monoclonal antibodies can be compared to control groups, which are otherwise treated and maintained in the same manner.

Anti-idiotypic monoclonal antibody treatment significantly increased the survival of animals bearing tumors and diminished lung metastasises.

The invention is further explained with the assistance of the following illustrative EXAMPLES.

EXAMPLE I

Generation of an anti-idiotypic antibody against P3 monoclonal antibody in a syngeneic model Female Balb/c mice, 6–8 weeks old, were immunized with two doses of 50 µg of purified P3 monoclonal antibody (anti-N-glycolyl-containing gangliosides)(Vázquez, A. M. et al. (1993) European Patent Application No. 657 471, ECACC accession number 94113026, Vázquez, A. M. etal, *Hybridoma*(1995) 14, 551–556) coupled to KLH, at 14 day intervals between doses.

Three days after the last immunization, the spleens of mice with high serum levels of Ab2 antibodies against P3 monoclonal antibody were removed and a cellular suspension was prepared by pressing the tissue through a stainless steel sieve or perfusing the spleen.

Fusion was performed by the method described by Kohler and Milstein (1975, *Nature* (London) 256, 495–497), with slight modifications.

Murine spleen cells were fused with the cells of the non-secreting murine myeloma P3/X63 Ag8 6.5.3, obtainable from European Collection of Animal Cell Cultures (ECACC), Centre for Applied Microbiology and Research Microbiological, Porton Down, Salisbury Wiltshire SP4, OJG, accession no. 85011420, in a ratio of 10:1, in 0.5 ml of fusion medium containing 42% polyethylene glycol in RPMI-1640 medium.

Fusion cells were cultivated in a HAT (hypoxanthine-aminopterin and thymidine) selective medium at 37° C. in a 5% $CO_2$ humid atmosphere.

Ten to fifteen days after fusion, the presence of antibodies in hybridoma supernatants was determined by ELISA (enzyme-linked immunosorbent assay). ELISA plates (high binding COSTAR) were incubated overnight at 4° C. with 10 µg/ml of P3 monoclonal antibody and other IgM antiganglioside monoclonal antibody, in carbonate-bicarbonate buffer having a pH of about 9.8.

The plates, were washed with PBS containing 0.05% TWEEN 20, and were then blocked with the same buffer, containing 1% BSA, for one hour at 37° C.

The washing step was repeated and 50µ/well of the supernatants were added. After incubating for 2 hours, the plates were washed again, and an alkaline phosphatase goat antimurine IgG Fc region conjugate antiserum was added. After washing, 100µ/well of the substrate solution (1 mg/ml of p-nitrophenylphosphate diluted in diethanolamine buffer, pH 9.8) was added. Absorbance was measured at 405 nm in an ELISA reader.

The capacity of the supernatants to block the binding of P3 monoclonal antibody to NeuGcGM3 was determined by an indirect ELISA performed on polyvinyl chloride activated plates (ICN-FLOW) with immobilized NeuGcGM3, according to the following method: Fifty microliters of the ganglioside in methanol (at a concentration of 4 µg/ml) were added to each well. Methanol was evaporated by placing the plates at 37° C. for one hour. Later, 150 µl of a TRIS-HCl 0.05 M pH 7.8 buffer containing 1% BSA were added to each well and the plates were incubated at 37° C. for 30 minutes.

Hybridoma supernatants were incubated with 4 µg/ml of P3 monoclonal antibody for 3 hours at 37° C. 50 µl of the mixture was then added to each well, and the plates were incubated at 37° C. for 90 minutes.

Each of the wells were washed 4 times with 200 µl of PBS, and 50 µl of alkaline phosphatase anti-mouse immunoglobulin conjugate antiserum, which was adequately diluted, was added. After washing with PBS, the wells were incubated with the substrate solution as described previously.

Figure 2:
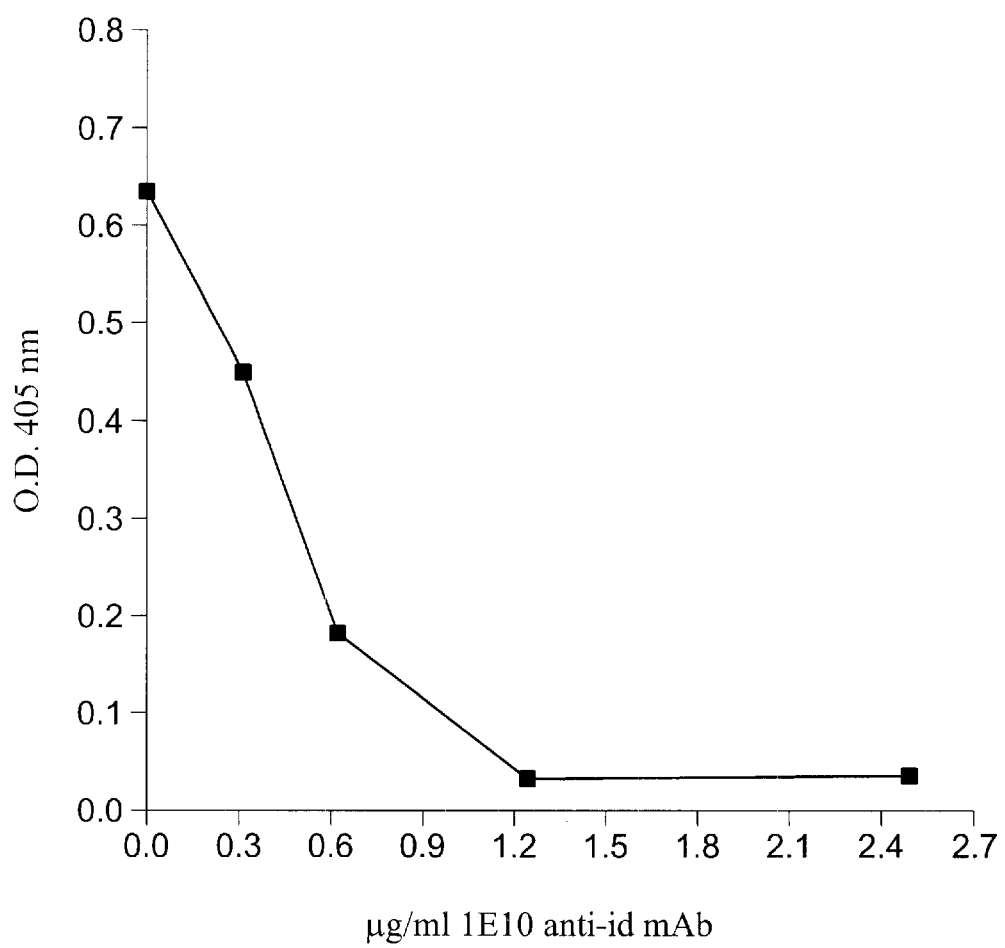
FIG. 2 shows the results of an inhibition assay where the P3 monoclonal antibody was incubated with the 1E10 anti-idiotype P3 monoclonal antibody, and later the reactivity of P3 monoclonal antibody to NeuGcGM3 was measured by ELISA.

An anti-idiotypic or anti-idiotype monoclonal antibody of the IgG1 subclass, named 1E10, was obtained. This 1E10 anti-idiotype P3 monoclonal antibody was very specific to the P3 monoclonal antibody used as the immunogen. It does not react with other antiganglioside antibodies, such as E1, A3 and F6 (FIG. 1). This anti-idiotypic monoclonal antibody was able to inhibit the binding of the P3 monoclonal antibody to NeuGcGM3 (FIG. 2) and to a P3 positive breast tumor cell line.

EXAMPLE II

Generation of anti-anti-idiotypic (Ab3) antibody response to 1E10 Anti-idiotype monoclonal antibody in a xenogeneic model.

Aluminum hydroxide-precipitated 1E10 anti-idiotype P3 monoclonal antibody was used to intradermally immunize Cynomolqus monkeys with a dose of 2 mg per injection of monoclonal antibody at 14 day intervals. The animals received several doses of the monoclonal antibody.

Serum samples were taken before and after the immunizations. The presence of Ab3 antibody response in monkey serum was determined by ELISA. ELISA plates (high binding COSTAR) were incubated overnight at 4° C. with 10 µg/ml of 1E10 monoclonal antibody or its F(ab')2 fragments in carbonate-bicarbonate buffer, pH 9.8.

After washing the plates with PBS containing 0.05% TWEEN 20, they were blocked with the same buffer, containing 1% BSA, for one hour at 37° C.

The washing step was repeated and 50 µl/well of the different serum dilutions were added. After incubating for 2 hours at 37° C., the plates were washed again and alkaline phosphatase goat anti-human immunoglobulin, anti-IgM or anti-IgG conjugate antisera were added. After washing, the substrate solution was added as previously described.

Blocking experiments were performed to distinguish between the anti-isotypic and anti-idiotypic antibody responses. Monkey serum was incubated overnight at 4° C. with 500 µg/ml of a monoclonal antibody with the same isotype as 1E10 monoclonal antibody, but with different specificity. The remnant serum reactivity against 1E10 monoclonal antibody was then measured by ELISA, as described above.

The monkey sera were checked for their ability to inhibit the binding of biotinilated P3 monoclonal antibody to 1E10 monoclonal antibody F(ab')2 fragments coated onto ELISA plates using the ELISA method described above. After incubating the coated plates with the serum dilutions, however, 50 µl of biotinilated P3 monoclonal antibody was added to each well. After incubating the plates for one hour at 37° C., the plates were washed and 50 µl of avidin-biotin-peroxidase complex was added to each well and incubated for one hour at 37° C. After washing, the substrate buffer (8 mg of o-phenylenediamine in 12 ml of phosphate-citrate buffer, pH 5.0) was added. Absorbance was measured at 492 nm in an ELISA plate reader.

Figure 3:
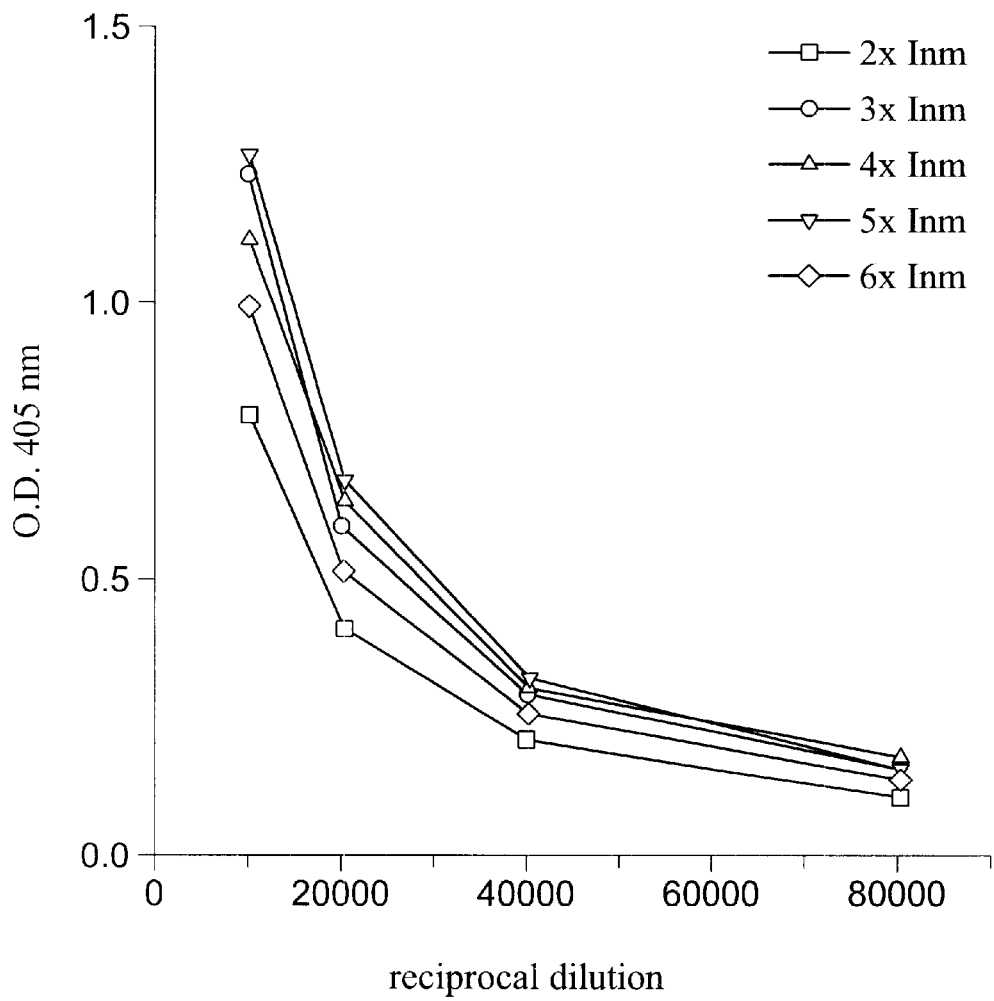
FIG. 3 shows the reactivity of monkey serum antibodies with 1E10 F(ab')2 fragments measured by ELISA after the animal received different doses of the aluminum hydroxide-precipitated 1E10anti-idiotype monoclonal antibody.
Figure 4:
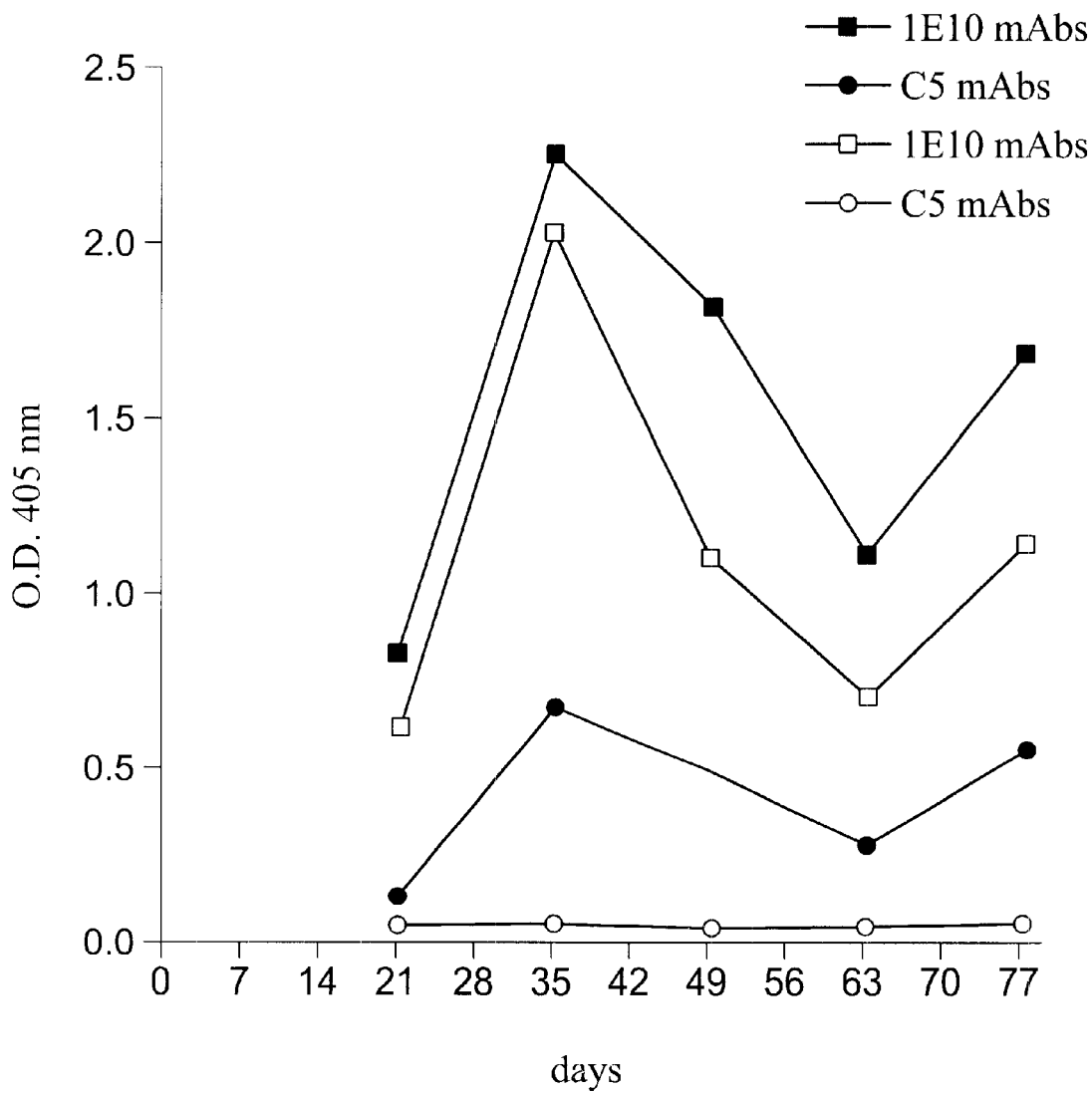
FIG. 4 shows the results of an inhibition assay where some of the monkey sera were incubated with an isotype matched irrelevant monoclonal antibody, while others were not, and the binding of serum antibodies to 1E10 monoclonal antibody and to the irrelevant monoclonal antibody were measured by ELISA. Arrows indicate the time of immunization and continue lines the times at which the animals were bled.
Figure 5:
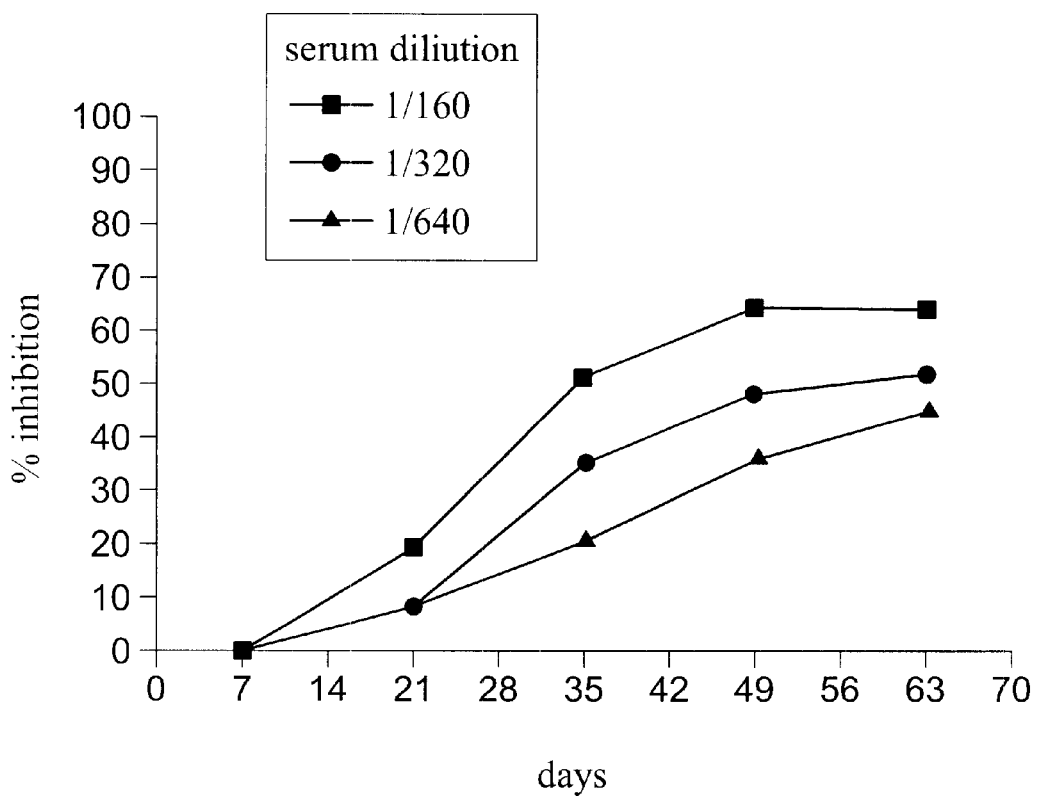
FIG. 5 shows the inhibition of P3 monoclonal antibody binding to 1E10 anti-idiotype monoclonal antibody by the serum of a monkey that was immunized with 1E10 monoclonal antibody, measured by ELISA. Arrows indicate time of immunization and continue lines the times at which the animals were bled.
Figure 6:
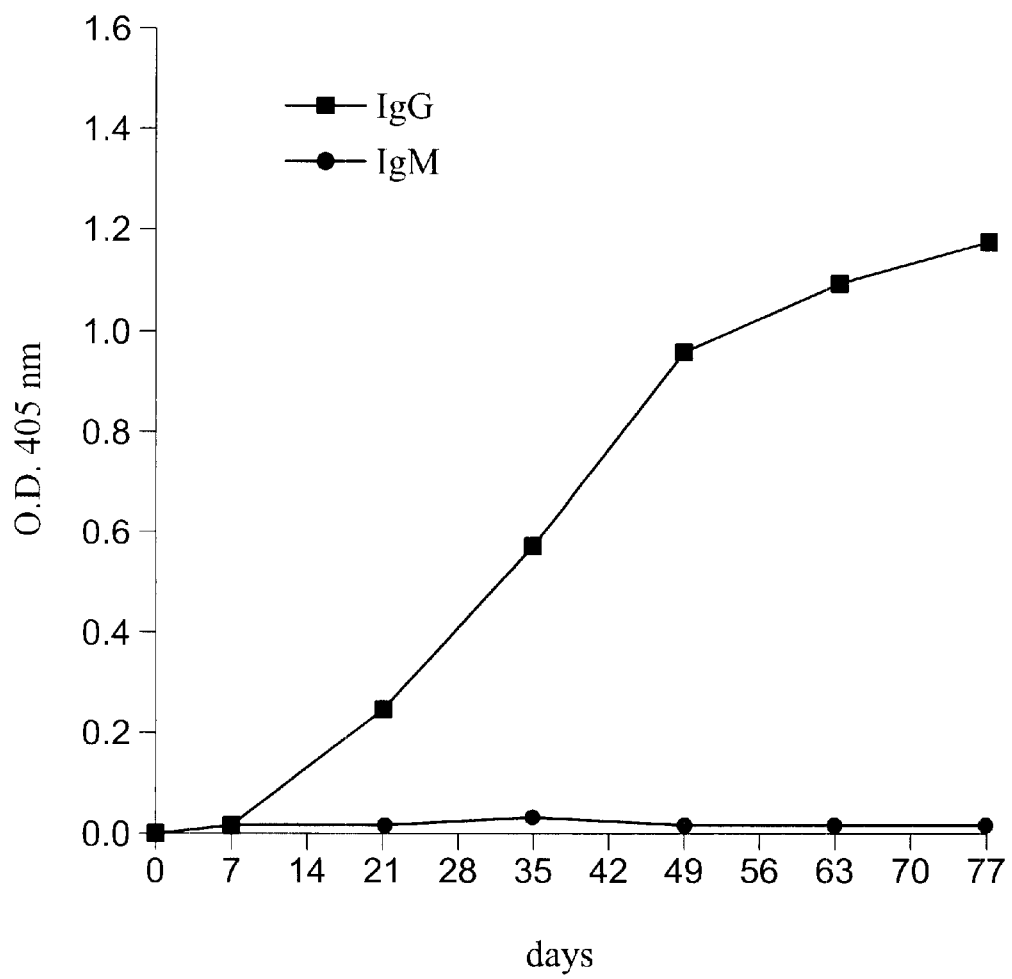
FIG. 6 shows the kinetic of IgM and IgG antibody response against 1E10 monoclonal antibody in the serum of a monkey that was immunized with the anti-idiotypic monoclonal antibody, measured by ELISA. Arrows indicate time of immunization and continue lines the times at which the animals were bled.
Figure 7:
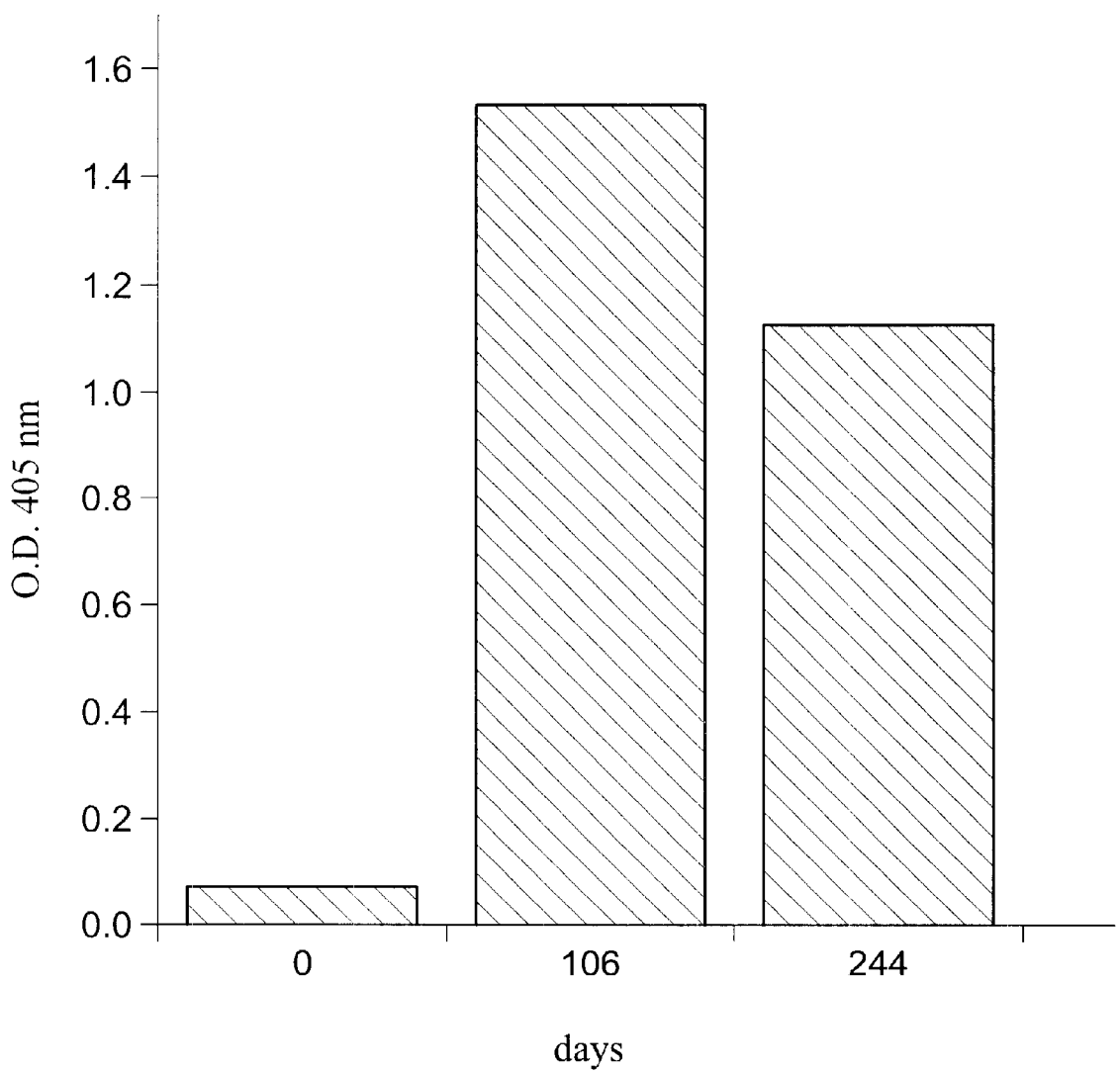
FIG. 7 shows the recognition of 1E10 F(ab')2 fragments by monkey pre-immune serum; by the serum obtained after the monkey received the last dose of aluminum hydroxide-precipitated 1E10 anti-idiotype monoclonal antibody (indicated with the arrow), and by the serum obtained 4 months after the animal received the last immunization.

Sera from monkeys that were immunized with 1E10 anti-idiotype P3 monoclonal antibody reacted strongly with 1E10 F(ab')2 fragments (FIG. 3). Sera from the immunized monkeys bound specifically to the immunized 1E10 monoclonal antibody, with less reactivity with unrelated monoclonal antibody (ior C5). The presence of antibodies against the 1E10 idiotype were confirmed after the animal sera were incubated with the irrelevant monoclonal antibody, due to a strong reactivity of the adsorbed sera with the 1E10 anti-idiotype P3 monoclonal antibody. Surprisingly, the induced anti-idiotypic antibody response was superior in comparison to the generated anti-isotypic antibody response (FIG. 4). Monkey Ab3 sera also inhibited the binding of biotinilated P3 monoclonal antibody to 1E10 anti-idiotype monoclonal antibody, indicating that monkey Ab3 sera share idiotopes with P3 monoclonal antibody (FIG. 5). A predominant IgG antibody response was generated against 1E10 antiidiotype P3 monoclonal antibody (FIG. 6). Sera from the monkeys reacted with 1E10 F(ab')2 fragments even 4 months. after the animals received the last immunization (FIG. 7). Ab3 antibodies with the inhibitory capacity of P3 which may bind to 1E10 were also detected at that time. No antibodies against NeuGcGM3 were detected in animal sera.

Thus it has been demonstrated that 1E10 anti-idiotypic monoclonal antibody is a gamma-type, since 1E10 anti-idiotypic monoclonal antibody is capable of inhibiting the binding of P3 monoclonal antibody with its antigen and is not able to induce the production of P3-like antibodies in the animals.

EXAMPLE III

Figure 8:
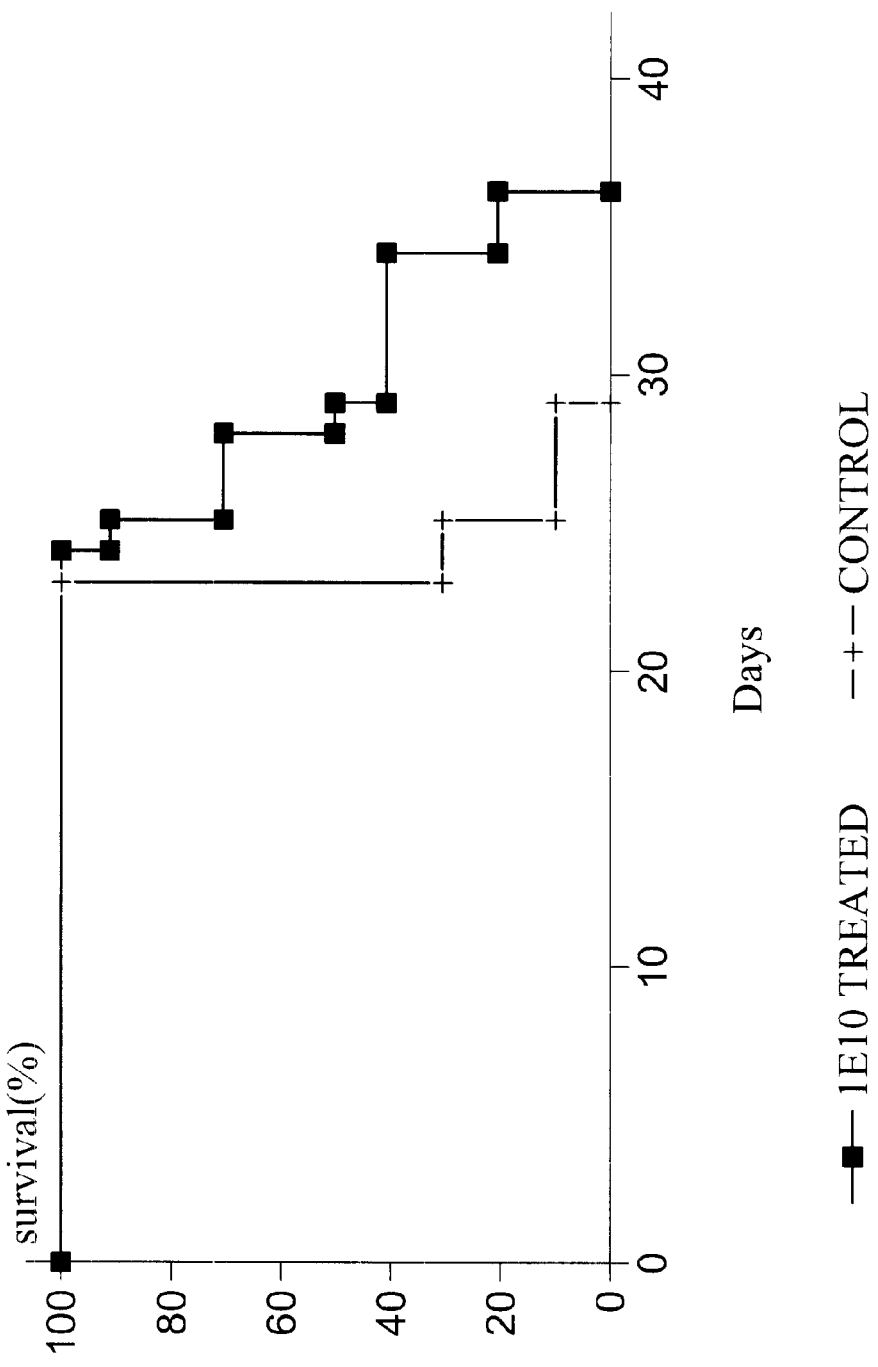
FIG. 8 shows Kaplan-Meyer curves for survival in mice treated with 1E10 anti-idiotypic or anti-idiotype P3 monoclonal antibody and inoculated with B16 melanoma cells.

Treatment of mice with 1E10 anti-idiotype monoclonal antibody C57BL/6 mice were immunized with five doses of 50 μg of aluminum hydroxide-precipitated 1E10 anti-idiotype P3 monoclonal antibody at 14 day intervals. One week later, the mice were injected subcutaneously with $5 \times 10^3$ B16 melanoma cells. Animals that were treated in the same way, but which did not receive the monoclonal antibody, were used as controls. Kaplan-Meyer survival curves are shown in FIG. 8, survival was significantly better in the group that was immunized with 1E10 anti-idiotype P3 monoclonal antibody than in the control group.

C57BL/6 mice were inoculated intravenously with $50 \times 10^3$ Lewis lung cancer cells. Fourteen days later, 10 μg of 1E10 was administered intravenously. After 6 days, mice were sacrificed and the number of lung metastases was counted. Animals treated with an irrelevant IgG monoclonal antibody or which received only PBS were used as controls. Seven of the 10 animals treated with 1E10 anti-P3 monoclonal antibody did not developed lung metastases. In the other 3 animals, the maximum total number of metastases was 3. In contrast, all the animals that were treated with the irrelevant IgG1 or that received only PBS developed lung metastases. These results indicate that the treatment with this gamma-type anti-idiotype monoclonal antibody had a protective effect against tumors.

The hybridoma that produces the monoclonal antibody identified as P3 was deposited with the European Collection of Cell Cultures, Centre for Applied Microbiology and Research & European Collection of Cultures (ECACC), Porton Down, Salisbury Wiltshire SP4, OJG, in accordance with the Budapest Treaty on Nov. 30, 1994, and was assigned accession no. ECACC 94113026.

The hybridoma that produces the monoclonal antibody identified as 1E10 was deposited with the European Collection of Cell Cultures, Centre for Applied Microbiology and Research & European Collection of Cultures, Porton Down, Salisbury Wiltshire SP4, OJG, in accordance with the Budapest Treaty on Nov. 29, 1997, and was assigned accession no. ECACC 97112901.

After being apprized of the monoclonal antibodies, hybridomas, and compositions containing the monoclonal antibodies according to the invention, other sources for the hybridomas and monoclonal antibodies will become readily apparent to those of skill in the art. For instance, spleen cells from goats, rabbits and other animals may be used in the fusion experiments to form a hybridoma that is within the scope of the present invention. Similarly, the monoclonal antibodies according to the present invention may be modified (e.g., "humanized"), or may otherwise be coupled to another molecule to decrease their antigenicity in human hosts or increase their effectiveness in protecting a host against malignant neoplasias, as known in the art.

Although the invention has been described with the aid of certain examples and embodiments, these are illustrative only, and the scope of the invention is to be determined by the appended claims.

What is claimed is:

1. A method of treating a malignant neoplasms of a mammal wherein a malignant cell expresses a ganglioside with a N-glycolyl moiety comprising:
    parenterally administering to said mammal a pharnaceutical composition comprising a pharmaceutically effective amount of an antibody 1E10, produced by the hybridoma deposited with the European Collection of Cell Cultures, Centre for Applied Microbiology and Research & European Collection of Cultures, Porton Down, Salisbury Wiltshire SP4, OJG, in accordance with the Budapest Treaty Nov. 30, 1994, and was assigned accession number ECACC 97112901.

2. The method according to claim 1 wherein the pharmaceutical composition further comprises a carrier selected from the group of carriers consisting of diluents, adjuvants, and transporting molecules.

* * * * *

UNITED STATES PATENT AND TRADEMARK OFFICE
CERTIFICATE OF CORRECTION

PATENT NO.    : 6,491,914 B1
DATED         : December 10, 2002
INVENTOR(S)   : Ana María Vázguez López et al.

It is certified that error appears in the above-identified patent and that said Letters Patent is hereby corrected as shown below:

Title page,
Item [75], Inventors, change "Maria" to -- María --, "Rodriguez" to -- Rodríguez --, and "Lopez" to -- López --

Column 1,
Line 14, change "Now" to -- now --
Line 41, change "(Id,)" to -- (Id.) --

Column 4,
Line 50, change "anti-Nlycolyl" to -- anti-N-glycolyl --

Column 5,
Line 54, change "be teen" to -- between --

Column 6,
Line 27, delete the period after "anti-idiotypic"

Column 7,
Line 21, change "etal" to -- et al --
Line 53, change "50µ/well" to -- 50µl/well --
Line 57, change "100µ/well" to -- 100µl/well --

Column 9,
Line 19, delete the period after "months"
Line 33, start a new paragraph after "antibody"

Column 10,
Lines 39-40, change "pharnaceutical" to -- pharmaceutical --

Signed and Sealed this

Second Day of September, 2003

JAMES E. ROGAN
*Director of the United States Patent and Trademark Office*